United States Patent [19]

Salzburg et al.

[11] 4,408,061

[45] Oct. 4, 1983

[54] PROCESS FOR THE PREPARATION OF 1,4-3,6-DIANHYDRO-HEXITOLS

[75] Inventors: Herbert Salzburg, Cologne; Holger Meyborg, Odenthal; Heinz Ziemann, Leichlingen, all of Fed. Rep. of Germany

[73] Assignee: Bayer Aktiengesellschaft, Leverkusen, Fed. Rep. of Germany

[21] Appl. No.: 357,353

[22] Filed: Mar. 11, 1982

[30] Foreign Application Priority Data

Mar. 20, 1981 [DE] Fed. Rep. of Germany ....... 3111092

[51] Int. Cl.$^3$ .......................................... C07D 493/04
[52] U.S. Cl. ..................................................... 549/464
[58] Field of Search ........................................ 549/464

[56] References Cited

U.S. PATENT DOCUMENTS 3,454,603 7/1969 Hartmann ........................... 549/464

FOREIGN PATENT DOCUMENTS 3041626 5/1982 Fed. Rep. of Germany .
3041673 6/1982 Fed. Rep. of Germany .

OTHER PUBLICATIONS

R. Montgomery and L. F. Wiggins, J. Chem. Soc., 1947, 433.
J. C. Goodwin, J. E. Hodge and D. Weisleder, Carbohyd. Res. 79, 133, (1980).
Fauconier, Bull. Soc. Chem., (1884), 41, 119.
L. F. Wiggins, J. Chem. Soc., 1945, 4.
Haworth, Heath and Wiggins, J. Chem. Soc., 1944, 155.
"Anhydrides of the Penitols and Hexitols", by L. F. Wiggins, in Advances in Carbohydrate Chemistry, 5 (1950), pp. 191 et seq.
"Alditol Anhydrides", by S. Soltzberg, in Advances in Carbohydrate Chemistry, 25 (1970), pp. 229 et seq.
Ropuszynski et al., Przem. Che. 48, (11), 665–668, 1969.
"Preparation of Bicyclic Hexitol Anhydride by Using Acidic Cation-Exchange Resin in a Binary Solvent", by J. C. Goodwin et al., in Carbohydrate Research, 79 (1980), pp. 133–141.

*Primary Examiner*—Richard Raymond
*Attorney, Agent, or Firm*—Gene Harsh; Joseph C. Gil; Richard A. Elder

[57] ABSTRACT

A process for the preparation of 1,4-3,6-dianhydro-hexitols from hexitols by elimination of water is described, characterized in that gaseous hydrogen halide is used as the acid dehydrating agent optionally with carboxylic acids, carboxylic acid halides and/or carboxylic acid anhydrides in quantities of up to 600 mol percent, based on the hexitols, as cocatalysts. The reaction is carried out in the absence of water and organic solvents, preferably using gaseous hydrogen chloride, temperatures of up to 300° C. and pressures of up to 250 bar. Very high yields are obtained after working up of the product by distillation or extraction.

11 Claims, No Drawings

PROCESS FOR THE PREPARATION OF 1,4-3,6-DIANHYDRO-HEXITOLS

This invention relates to an improved process for the preparation of 1,4-3,6-dianhydrohexitols by the intramolecular elimination of water using gaseous hydrogen chloride, optionally in the presence of cocatalysts based on organic carboxylic acids, carboxylic acid chlorides and/or carboxylic acid anhydrides in the absence of both solvents and water.

BACKGROUND OF THE INVENTION 1,4-3,6-dianhydro-hexitols constitute a series of compounds which have been known since about 1880 and have been described in:

1. Fauconier, Bull Soc. Chem. (1884) 41, 119;
2. L. F. Wiggins, J. Chem. Soc. 1945, 4;
3. Haworth, Heath and Wiggins, J. Chem. Soc. 1944, 155;
4. R. Montgomery and L. F. Wiggins, J. Chem. Soc. 1947, 433, and
5. J. C. Goodwin, J. E. Hodge and D. Weisleder, Carbohyd. Res. 79, 133 (1980).

It is a common feature of the syntheses of these compounds that they are carried out in solvents, the intramolecular elimination of water from the hexitols being brought about by acid substances. The solvent-free syntheses also known in the literature make use of marginally volatile acids such as, e.g., sulfuric acid.

The following table gives a representative summary of various solvents and catalysts used and illustrates the efficiency of the synthesis method when used to produce 1,4-3,6-dianhydro-mannitol (the dextro isomer of which is commonly called isomannide in the literature and represented by the structure

| Solvent/Catalyst | Yield of Isomannide | Literature |
|---|---|---|
| Dichloroglycerol | ~36% | (2) |
| Conc. Hydrochloric acid | 35% | (3) |
| Conc. Hydrochloric acid | 40% | (3) |
| Conc. Hydrochloric acid | 25% | (4) |
| Ethylacetate/dioxane | 35% | (5) |

The main disadvantages of the above processes lie in the unsatisfactory yields and correspondingly large quantities of resin-like distillation residues produced and in the long reaction times frequently required (up to 85 hours). These disadvantages eliminate the possibility of preparing, for example, isomannide or isosorbide (1,4-3,6-dianhydro-D-sorbitol of the formula

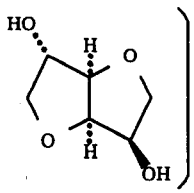

on a large technical scale, particularly since the raw material cost of mannitol and sorbitol required as starting compounds is considerable when compared with the usual cost of starting materials in the chemical industry.

It was, therefore, an object of the present invention to improve the preparation of dianhydrohexitols ("isohexitols" or dianhydro-hexites) from hexitols. It was intended, in particular, that the yield should be substantially higher than that obtained in known processes in order to provide the possibility of economically-acceptable production of dianhydro-hexitols on an industrial scale.

It has now surprisingly been found that in the process according to the present invention isohexitols are obtainable from hexitols in high yields by an unexpectedly selective reaction if the use of solvents is eliminated and a gaseous hydrogen halide, preferably hydrogen chloride, is reacted with crystalline or syrupy hexitol.

DESCRIPTION OF THE INVENTION

The present invention thus relates to a process for the preparation of 1,4-3,6-dianhydrohexitols from the corresponding hexitol characterized in that a gaseous hydrogen halide is used as an acid dehydrating reagent and organic carboxylic acids, carboxylic acid halides and/or carboxylic acid anhydrides are optionally used as cocatalysts, where the reaction is carried out in the absence of both water and organic solvents.

The reaction may be carried out at normal pressure or, preferably, at an elevated pressure of 1 to 250 bar and, most preferably at 1 to 40 bar. The components are reacted together at a temperature of 0° to 300° C., preferably 20° to 160° C. and, most preferably, 30° to 140° C. Other hydrogen halides such as HBr and HF may also be used for the elimination of water, with HBr also providing advantageous yields.

Particularly suitable for the selectivity of the dehydration reaction is a cocatalysis of organic carboxylic acids, carboxylic acid halides and symmetric or asymmetric carboxylic acid anhydrides. The quantities of cocatalysts used may vary within wide limits and can range from 0.1 to 600 mol percent, preferably from 0.5 to 10 mol percent and, most preferably, from 1 to 4 mol percent, based on the hexitols.

If an acid chloride is used as a cocatalyst, then the addition of HCl may be omitted, if by reaction of the acid chloride with the OH-groups of the hexitol the corresponding quantity of hydrogen-chloride is liberated.

Carboxylic acids of the general formula R—(-ROOH)$_x$ wherein x=1 to 6 and R denotes an x-valent residue of a saturated or unsaturated aliphatic carboxylic acid or of an aromatic or araliphatic carboxylic acid, are preferably used as the cocatalysts. Examples of suitable acids include formic acid, acetic acid, adipic acid, succinic acid, oxalic acid, maleic acid, phthalic acid, benzoic acid, phenyl acetic acid, chloroacetic acid, trifluoroacetic acid or carbonic acid.

Useful carboxylic acid halides include halides of the above-mentioned carboxylic acids corresponding to the general formula:

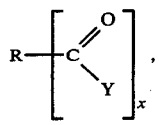

wherein
Y=halogen, e.g., chlorine or bromine, and
x and R have the meaning indicated above.

Examples of suitable acid halides include acetyl chloride, adipoyl chloride, hexanoyl chloride, oxalyl chloride, benzoyl chloride and phenyl acetyl chloride.

Symmetric or asymmetric carboxylic acid anhydrides of the acids of the above formula wherein x=1 to 6 and R denotes identical or different groups having the meaning indicated above may also be used. Examples of such acid anhydrides include acetic anhydride, succinic acid anhydride, adipic acid polyanhydride, phthalic acid anhydride and similar compounds.

In the process according to the invention, the dehydrating reaction is carried out by introducing the gaseous hydrogen chloride into the solid, liquid or molten hexitol in equivalents of up to about 1000 times (e.g. 0,01 to 1000 times) per equivalent of hexitol, but preferably up to saturation point of the hexitol at the appropriate temperature and pressure, most preferably in the equivalent or up to 1000 times the equivalent ratio. The cocatalysts (when used) are preferably mixed with the hexitols in an amount of from 0.1 to 600 mol percent, preferably from 0.5 to 10 mol percent, most preferably from 1 to 4 mol percent, based on the hexitols, before the hydrogen chloride is added.

The isohexitols may then be isolated by fractional distillation in which case water and cocatalysts are obtained while the reaction is running to completion, and the 1,4-3,6-dianhydrohexitol is subsequently obtained in a water jet vacuum or high vacuum. In the alternative, the reaction product may be worked up by extraction or distillation after neutralization of the halide in the reaction mixture with bases such as, for example, sodium hydroxide or triethylamine. After reaction of the hexitol with hydrogen chloride, all the active chloride (HCl or acid chloride) may be neutralized with inorganic bases such as NaOH, KOH, Ca(OH)₂ or Ba(OH)₂, or with organic bases, such as trialkylamines or pyridines. The dianhydro-hexitols subsequently isolated by extraction or, preferably, by distillation, are obtained in high yields in crystalline form with a high degree of purity.

The 1,4-3,6-dianhydro-hexitols thus obtained are valuable components for the diisocyanate polyaddition process and may be used as starters for polyethers, for example, by the addition of ethylene oxide and/or propylene oxide; as components for polyesters; as a starting polyol for polycarbonates; and as hardeners for epoxide resins.

In the examples which follow, the quantities of compounds used are given in parts by weight.

EXAMPLES

Example 1

400 Parts of D-mannitol and 20 parts of acetic acid are heated to 120°–140° C. and hydrogen chloride is introduced into the mixture until the mixture is saturated without further external heating. When the uptake of gas has been completed (after about 150 minutes), stirring is continued for an additional 30 minutes at the final temperature reached of approximately 140° C., and water and acetic acid are distilled off at the same time. The residue is then fractionally distilled under vacuum. Isomannide (1,4-3,6-dianhydro-D-mannitol) distills in a water jet vacuum at 155° to 165° C. and 15 to 18 bar, or in an oil pump vacuum at 145° C./0.15 bar, and is obtained in a yield of 65% of the theoretical with a melting point of 83° to 85° C.

For comparison, the yield obtained in literature reference (2) is 36% of the theoretical.

Example 2

400 Parts of D-mannitol and 20 parts of acetyl chloride are subjected to 40 bar of hydrogen chloride at room temperature in a pressure reactor and then heated to 50° C. while the pressure is maintained at 40 bar by forcing in fresh hydrogen chloride. When no further fall in pressure is observed (after about 110 minutes), the pressure is maintained for an additional 30 minutes while stirring is continued, then the pressure is released at room temperature and the product is fractionated under vacuum. The yield of isommanide is 80 to 85% of the theoretical.

Example 3

364 Parts of D-sorbitol and 20 parts of glacial acetic acid are subjected to 40 bar of hydrogen chloride in a pressure vessel for 40 hours at 45° C. The reaction mixture is then fractionated. After removal of water and acetic acid by distillation at normal pressure, 247 parts (84.5% of the theoretical amount) of 1,4-3,6-dianhydro-sorbitol are obtained at 165° to 175° C. and 17 to 18 bar in the form of an oil which rapidly crystallizes and has a melting point of 54.5° to 55.5° C.

Example 4 (General Method)

400 g of hexitol and 5 mol percent of an organic carboxylic acid or an organic carboxylic acid anhydride or an organic carboxylic acid halide are added 80 g of hydrogen chloride into a pressure reactor at room temperature and then heated to 100° C. After 3 hours at 100° C. the pressure is released at room temperature and the reaction mixture is neutralized with half concentrated sodium hydroxide solution at 20° to 40° C., using bromophenol blue as indicator, until no further colour change from blue to yellow takes place. The reaction mixture is then fractionally distilled or exhaustively extracted with ethyl acetate. The product solution obtained by extraction is concentrated by evaporation to separate the product which is then optionally distilled under vacuum. Yields of 70 to 85% of the theory are obtained.

| Starting material | p (HCl) bar | yield % |
|---|---|---|
| Sorbit | 1 | 79, extracted + distilled |
| " | 40 | 84, distilled |
| Mannit | 5 | 70, |

| Starting material | p (HCl) bar | yield % | |
|---|---|---|---|
| " | 40 | 82, | and redistilled |
| " | 40 | 78, | |

What is claimed is:

1. In a process for the preparation of 1,4-3,6-dianhydro-hexitols from hexitol comprising splitting off of water by means of strong acids, the improvement wherein gaseous hydrogen halide is used as the acid and the reaction is carried out in the absence of both water and organic solvents.

2. A process according to claim 1, characterized in that organic carboxylic acids, carboxylic acid halides and/or carboxylic acid anhydrides are used as cocatalysts.

3. A process according to claim 1, characterized in that hexitols in the form of solids, liquids or melts are treated with gaseous hydrogen chloride in an amount ranging from an equivalent ratio to 1000 times the equivalent ratio.

4. A process according to claim 2, characterized in that the hexitols are treated with the gaseous hydrogen chloride in the presence of cocatalysts added in a proportion of 0.1 to 600 mol percent, based on the hexitols.

5. A process according to claim 1, characterized in that the reactants are reacted at a temperature of 0° to 300° C. and a pressure of 1 to 250 bar.

6. A process according to claim 1, characterized in that a cocatalyst is used in a proportion of 0.5 to 10 mol percent, based on the hexitol, and the reactants are reacted at a temperature of 20° to 160° C. and a pressure of 1 to 40 bar.

7. A process according to claim 1, characterized in that the hydrogen chloride is introduced into the reaction mixture until saturation is reached.

8. A process according to claim 1, characterized in that carboxylic acids of the general formula $$R-(ROOH)_x$$

wherein
x = 1 to 6 and
R = a residue of a saturated or unsaturated aliphatic carboxylic acid or of an aromatic or araliphatic carboxylic acid, and/or symmetric or asymmetric carboxylic acid anhydrides are used as cocatalysts for the reaction.

9. A process according to claim 1, characterized in that carboxylic acid halides of the general formula

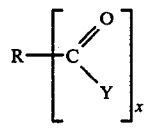

wherein
x = 1 to 6,
Y = a halogen, and
R = residue of a saturated or unsaturated aliphatic carboxylic acid or of an aromatic or araliphatic carboxylic acid, are used as cocatalysts for the reaction.

10. A process according to claim 1, characterized in that after the reaction of the hexitols with hydrogen chloride, the resulting dianhydro-hexitol is isolated by fractional distillation under vacuum.

11. A process according to claim 1, characterized in that after the reaction of the hexitols with hydrogen chloride, all the active chloride is neutralized with inorganic or organic bases and then the dianhydro-hexitol is isolated by extraction and/or distillation.

* * * * *